United States Patent [19]

Scarberry

[11] Patent Number: 5,009,635

[45] Date of Patent: Apr. 23, 1991

[54] PUMP APPARATUS

[75] Inventor: Eugene N. Scarberry, Trafford, Pa.

[73] Assignee: Respironics Inc., Murrysville, Pa.

[21] Appl. No.: 432,159

[22] Filed: Nov. 6, 1989

[51] Int. Cl.$^5$ .............................................. A61M 1/00
[52] U.S. Cl. ........................................ 604/27; 604/30; 604/37
[58] Field of Search ................. 604/19, 27, 30, 37, 604/35, 246, 247

[56] References Cited

U.S. PATENT DOCUMENTS

| 15,192 | 6/1856 | Peale . | |
|---|---|---|---|
| 179,950 | 7/1876 | Parsons . | |
| 386,603 | 7/1888 | Parsons . | |
| 451,179 | 4/1891 | Ware . | |
| 598,407 | 2/1898 | Armstrong . | |
| 1,925,230 | 9/1933 | Buckhout | 604/37 X |
| 2,064,619 | 12/1936 | Leonard et al. . | |
| 3,133,696 | 5/1964 | Mirando | 230/160 |
| 3,463,159 | 8/1969 | Heimlich . | |
| 3,780,736 | 12/1973 | Chen | 604/30 |
| 3,892,226 | 7/1975 | Rosen | 604/37 X |
| 4,607,663 | 8/1986 | Raftis et al. | 137/846 |

OTHER PUBLICATIONS

Denver Pleuro-Peritoneal Shunt, 1985, published by Codman & Shurtleff, Inc.

Primary Examiner—John D. Yasko
Attorney, Agent, or Firm—Carothers & Carothers

[57] ABSTRACT

A pump apparatus such as a stomach pump or the like having a variable volume pumping chamber in the form of a resiliently flexible bulb with a one way flow check valve disposed within the bulb to preclude backflow therefrom, and a second check valve downstream of the resilient bulb, preferably within a reservoir to preclude backflow from the reservoir to the pumping chamber and to contain pumped matter within the reservoir.

13 Claims, 1 Drawing Sheet

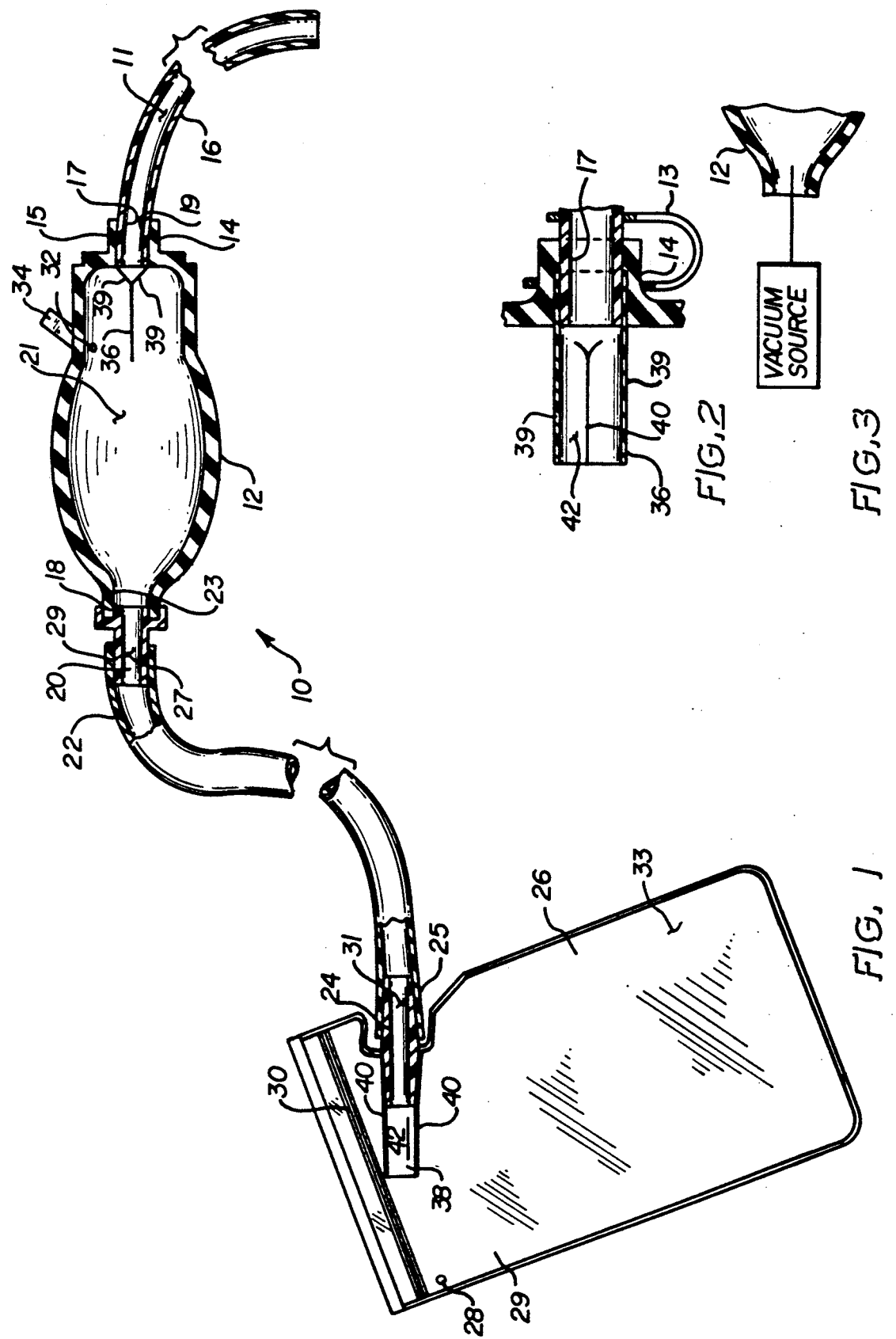

PUMP APPARATUS

BACKGROUND OF THE INVENTION

In the art of pumps such as stomach pumps and the like, it is well known to provide a manually operable pumping apparatus which includes a squeeze bulb having valve elements which operate under the impetus of fluid pressure within the pumping apparatus to provide for unidirectional flow within the pumping apparatus. For example, a stomach pump of the type characterized is known to have such a bulb and check valve elements at the inlet and outlet of the resilient bulb to provide for a positive flow pumping action as shown in U.S. Pat. No. 598,407. Other such pumps or syringe apparatus are disclosed by U.S. Pat. Nos. 386,603 and 179,950.

Also known is a pump apparatus for use as a pleuroperitoneal shunt which includes a flexible pump chamber containing two miter valves therein, the pump chamber being disposed between two lengths of catheter. Such a shunt apparatus is offered by Denver Biomaterials Inc., for example.

One way flow check valves for use in medical and other apparatus for such purposes as stomach pumping, drainage of the chest, apparatus inflation, and a variety of other purposes are disclosed in U.S. Pat. Nos. 3,463,159, 15,192, 3,133,696, and 4,607,663. Still other syringe or air bulb structures are disclosed in U.S. Pat. Nos. 2,064,619 and 451,179.

BRIEF SUMMARY OF THE INVENTION

I have invented a novel and improved squeeze bulb type pump, for use as a stomach pump for example, in which the pumping impetus is provided by manual squeezing of a resiliently flexible squeeze bulb which has defined therein a variable volume pumping chamber. Within the variable volume pumping chamber is disposed an inlet one way flow check valve for permitting inflow of material being pumped as the squeeze pump resiles and the chamber therewithin expands in volume. The inlet check valve disposed within the squeeze bulb chamber closes upon manual squeezing of the squeeze bulb to preclude backflow of material from the bulb chamber toward the locale from which it was originally pumped.

The invention also contemplates a one way flow check valve element disposed within a reservoir that is connected to an outlet end of the squeeze bulb. This outlet check valve element is closed while the pumping chamber volume expands as the squeeze bulb resiles, thus preventing backflow of material from the reservoir to the squeeze bulb. Upon manual squeezing of the squeeze bulb the outlet check valve opens to accommodate flow from the squeeze bulb into the connected reservoir. The reservoir thus is adapted to receive and contain material from the squeeze bulb. The reservoir also contemplates inclusion of a vent to ventilate gases from the reservoir, and a selectively operable opening which may be utilized to open the reservoir for disposal of its contents or to seal the reservoir to contain the contents therein.

The invention provides a novel and improved stomach pump or the like having greatly enhanced volumetric efficiency, ease of manual operation, improved volume per stroke pumping capability, rapid pressure draw down for enhanced suction pumping capability, and a remote, removable reservoir with an included non-return flow check valve, among other features and advantages.

It is accordingly one object of the invention to provide a novel and improved stomach pump or the like.

A more specific object of the invention is to provide a novel stomach pump operable by manual actuation of a resilient squeeze bulb to draw material through an inlet and subsequently pass such material to a connected reservoir where the material passes through a non-return flow check valve in its passage into the reservoir.

These and other objects and further advantages of the invention will be more readily appreciated upon consideration of the following detailed description and the accompanying drawings, in which:

FIG. 1 is a partially sectioned side elevational of a stomach pump according to one presently preferred embodiment of the instant invention;

FIG. 2 is a fragmentary portion of FIG. 1 showing operation of a one way flow check valve; and FIG. 3 is a schematic view showing an alternative embodiment of the invention.

There is generally indicated at 10 in FIG. 1 a stomach pump or the like according to one presently preferred embodiment of the instant invention and comprising a resililently deformable pumping bulb 12 of rubber for example, which is connected at an inlet end 14 thereof to a preferably pre-shaped, elongated tubular member 16 of a structure and material, suitable plastic for example, to maintain a predetermined shape or form. Tubular member 16 thus is suitably connected to bulb 12, for example by having one end 17 thereof inserted within an inlet opening 19 in the inlet end 14 of bulb 12 so that a through passage 11 in tube 16 communicates with an interior space 21 defined within bulb 12. In an alternative embodiment, a suitable fitting (not shown) may be mounted to tube end 17 to engage the outer periphery 15 of bulb inlet end 14. In addition, a retention tab 13 (FIG. 2) may be utilized to retain tube end 17 adjacent to bulb inlet 14 even when the tube end 17 and bulb inlet 14 are disengaged.

An outlet opening 23 is formed adjacent an opposed or outlet end 18 of bulb 12 to communicate with interior space 21, and an elongated coupling or connector element 20 engages opening 23 to provide fluid flow communication into one end 29 of an elongated conduit 22 via a through opening 27 formed in connector 20. The opposed end 25 of conduit 22 is connected to a coupling 24 for fluid flow communication via a through opening 31 formed therein. Coupling 24 is connected in fluid flow communication to a reservoir 26 which receives matter pumped by bulb 12 through conduit 22.

Couplings 20 and 24 may include tapered exterior end portions which are received in friction fit within the respective openings in the connected components as above described to form sealed flow junctions between bulb 12, conduit 22 and reservoir 26 as above described. Of course, couplings 20 and 24 may take any of a variety of alternative forms suitable for connection of the conduit 22 in fluid flow communication between outlet 18 of bulb 12 and the inlet to reservoir bag 26. Included among such alternatives are coupling elements formed as an integral part of the bulb 12 and the reservoir 26. In particular, the reservoir bag 26 may have a foreshortened length of conduit, not shown, which is preferably formed integrally with reservoir 26. The foreshortened conduit may have an open free end similar in all salient respects to the conduit end portion 29 above described for direct connection of reservoir 26 to bulb 12 without any substantial length of intervening conduit extending therebetween.

Reservoir 26 comprises a flexible bag-like structure, a plastic bag for example, having an air vent 28 located adjacent an upper region 29 thereof to ventilate gases from an interior space 33 defined within reservoir 26. A selectively operable opening structure 30 may be included to permit selective opening and closing of reservoir 26 to either retain the contents thereof within space 33, or to selectively dispose of the contents therein. Reservoir 26 may be a plastic bag, as noted, having an opening structure 30 in the nature of interengaging elongated bead and groove structures as in some known plastic bags. Alternatively, or in addition, a drain opening formed as a length of flexible tubing (not shown) extending from reservoir 26 may be provided. The flexible tubing preferably is located in a lower region of the plastic bag, and is folded back upon itself and suitably clamped as by being tightly encompassed by elastic bands to close the reservoir drain opening and retain the contents.

To provide effective pumping action, the invention further contemplates a system of vents and check valves as follows. A vent opening 32 is provided, for example near upstream end of bulb 12, or alternatively in tube 16 adjacent to bulb inlet end 14, which vent 32 may be selectively opened and closed as by a cover element 34, for example a strip of self-adhering tape affixed to the exterior of bulb 12 to cover vent opening 32. A check valve 36 of a known structure is provided within space 21 in bulb 12 adjacent inlet end 14 thereof in fluid flow communication with passage 11 of tube 16 such that material drawn into space 21 by the pumping action of bulb 12 passes through the length of passage 11 in tube 16 and thence through valve 36 and into space 21.

In FIG. 1, valve 36 is shown in its closed configuration whereas in FIG. 2 it is shown in its open configuration. From these showings of valve 36 it will be appreciated that the valve per se is similar to valves shown in the prior art, such as in above cited U.S. Pat. No. 3,463,159. Thus, it will be apparent that valve 36 permits flow only in the direction through passage 11 in tube 16 toward inlet 14 and into space 21, and closes upon exertion of any flow impetus in the opposed direction.

A further entirely similar check valve structure 38 is disposed within reservoir bag 26 and is connected to coupling 24 to pass material into space 33 within reservoir 26. Valves 38 and 36 both are preferably comprised of generally planer, adjacent membranes 39 which are joined along a pair of laterally spaced, elongated jointlines 40 to define a variable cross-sectional area opening 42 to pass matter including solid particles upon application of flow impetus in one direction, and which membranes 39 collapse upon one another to close such opening to flow therethrough, even if solid particles are present between the collapsed membranes, upon application of flow impetus in the opposed direction. In the structure as above described, both of valves 36 and 38 permit flow only toward reservoir 26. For further particulars of valves 36 and 38, reference is made hereby to U.S. Pat. No. 3,463,159 of Heimlich, and said U.S. Pat. No. 3,463,159 is hereby incorporated herein and made a part hereof by reference.

From the above description, the operation of my novel stomach pump will be readily appreciated. The tube 16, being preferably pre-shaped to accommodate insertion thereof into the upper trachea of a patient, permits repeated manual squeezing of resilient bulb 12 to draw material by suction from the patient's stomach via tube 16 and into space 21. A manual compression cycle of bulb 12 closes valve 38 and forces material within space 21 to move toward reservoir 26. Such material upon reaching reservoir 26 passes via open check valve 38 into the reservoir space 33 whereas the gases flowing therewith along the same flow path may be vented via vent 28. Upon each release of a manual compression of bulb 12, the bulb resiles firmly and quickly to a fully expanded state. In the process material is drawn via tube 16 and open valve 36 into space 21 as valve 38 remains closed. Repeated cycles of manual compression and spontaneous expansion of bulb 12 thus produces a pumping action which moves material along a unidirectional flow path toward a reservoir. At any point during operation of the stomach pump as described, the pumping action may be stopped and the reservoir bag 26 may be removed and replaced by another reservoir bag 26. The action of check valve 42 retains the contents of reservoir 26 such that the additional measure of closing vent 28 as with a piece of self-adhering tape or the like is all that is necessary to create from reservoir bag 26 a sealed containment that may be used to transport the contents to a hospital or clinic, or to maintain containment of the contents for disposal.

The combination of the removable flexible reservoir, the resilient bulb, and the removable preformed tube element with retainer provides an advantageously compact and utilitarian stomach pump. In one contemplated use environment such as in EMS units, for example, the tube 16 and bulb 12 may be separated and folded together, the mutually engageable connection portions thereof being retained in closely adjacent proximity by tab 13. The disengaged tube and bulb assembly then are stowed within reservoir bag 26 so that prior to use the stomach pump 10 is a compact, self-packaged apparatus. To prepare the stomach pump for use, it is necessary only to open the closure 30 of reservoir bag 26, remove bulb 12 and tube 16, engage the end portion 17 of tube 16 in fluid flow communication with bulb inlet 14, and similarly engage the bulb outlet 18 with the inlet to reservoir bag 26 as described. After use, the bag 26 may be suitably disposed of and the inlet tube and bulb assembly may be disconnected, cleansed, and repackaged in a new reservoir bag 26.

It is also contemplated to use bulb 12 itself as a reservoir by connecting coupling 20 to a vacuum source (FIG. 3). The vacuum drawn thereby will be effective to draw material via tube 16 into space 21, and for such use vent 32 is opened or closed as needed to control the magnitude of the vacuum produced by the vacuum source within bulb 12.

From the above description it will be appreciated that I have invented a novel and improved stomach pump or the like. The above description contemplates only presently preferred embodiments of the invention, but I have contemplated various alternative and modified embodiments other than disclosed hereinabove, and certainly such would also occur to others versed in the art once apprised of my invention. Accordingly, the invention is to be construed broadly and limited only by the scope of the claims appended hereto.

I claim:

1. A stomach pump or the like comprising:
   a resiliently flexible bulb means enclosing an interior space and having an outlet and an inlet communicating between said interior space and the exterior of said bulb means;

first one-way flow check valve means disposed in fluid flow communication with said inlet and operable to preclude material movement from said interior space via said inlet;

first connector means disposed adjacent said outlet;

a remote reservoir means for receiving material therewithin and including a second connector means disposed in fluid flow communication therewith to permit movement of material into said reservoir means;

selectively releasable means connecting said first and second connector means to permit material to move from said interior space of said bulb means into said remote reservoir means; and said reservoir means including second one-way flow check valve means disposed in fluid flow communication with said second connector means and operable to preclude movement of material from within said reservoir means via said second connector means.

2. The stomach pump as set forth in claim 1 wherein said first one-way flow check valve means is disposed within said interior space.

3. The stomach pump as set forth in claim 2 wherein said reservoir means includes a vent means for venting gas therefrom.

4. The stomach pump as set forth in claim 3 wherein said reservoir means includes an opening means which is selectively operable to open or close said reservoir means to thereby selectively retain or dispose of the contents thereof.

5. The stomach pump as set forth in claim 4 wherein said reservoir means is a flexible bag means.

6. The stomach pump as set forth in claim 1 additionally including an elongated tube means releasably connected in fluid flow communication with said inlet means.

7. The stomach pump as set forth in claim 6 wherein said elongated tube means is a pre-shaped tube adapted to be received into the upper trachea of a patient.

8. The stomach pump as set forth in claim 1 wherein said bulb means is operable, upon resilient deformation thereof which reduces the volume of said interior space, to move material within said interior space outwardly thereof only via said outlet.

9. The stomach pump as set forth in claim 8 wherein said bulb means is operable, upon resiling thereof which increases the volume of said interior space, to move material inwardly thereof into said interior space only via said inlet.

10. The stomach pump as set forth in claim 9 wherein said first and second one-way flow check valve means each includes a pair of adjacent, generally planer flexible valve elements which are joined at least along a pair of laterally spaced elongated joint lines to form an elongated variable cross section passage extending therebetween laterally intermediate said joint lines.

11. The stomach pump as set forth in claim 9 wherein said bulb means includes a vent opening for controlling the movement of material into said interior space upon resiling of said bulb means.

12. The stomach pump as set forth in claim 6 additionally including retention means for retaining said elongated tube means with respect to said inlet means when said tube means is disconnected from fluid flow communication with said inlet means.

13. The stomach pump as set forth in claim 12 wherein said reservoir means includes closure means for selectively opening and closing said reservoir means in a manner that said elongated tube means and said bulb means may be received within said reservoir means.

* * * * *